US008298140B2

(12) United States Patent
Beck-Nielsen et al.

(10) Patent No.: US 8,298,140 B2
(45) Date of Patent: Oct. 30, 2012

(54) ANALYSIS OF EEG SIGNALS TO DETECT HYPOGLYCAEMIA (75) Inventors: Henning Beck-Nielsen, Nyborg (DK); Rasmus Elsborg Madsen, Charlottenlund (DK)

(73) Assignee: Hypo-Safe A/S, Lyngby (DK)

( * ) Notice: Subject to any disclaimer, the term of this patent is extended or adjusted under 35 U.S.C. 154(b) by 913 days.

(21) Appl. No.: 12/308,014

(22) PCT Filed: Jun. 7, 2007

(86) PCT No.: PCT/EP2007/055628
§ 371 (c)(1),
(2), (4) Date: Dec. 4, 2008

(87) PCT Pub. No.: WO2007/144307
PCT Pub. Date: Dec. 21, 2007

(65) Prior Publication Data
US 2009/0287107 A1  Nov. 19, 2009

(30) Foreign Application Priority Data

Jun. 15, 2006 (GB) .................................. 0611872.3

(51) Int. Cl.
*A61B 5/00* (2006.01)
*A61B 5/02* (2006.01)
*A61B 5/04* (2006.01)
(52) U.S. Cl. ........ 600/300; 600/508; 600/544; 128/920; 128/925
(58) Field of Classification Search .................. 600/300, 600/508, 544; 128/920, 925
See application file for complete search history.

(56) References Cited

U.S. PATENT DOCUMENTS

| | | | |
|---|---|---|---|
| 3,195,533 A | | 7/1965 | Fischer |
| 3,760,796 A * | | 9/1973 | Baessler et al. ............... 600/544 |
| 4,608,635 A | | 8/1986 | Osterholm ................... 364/414 |
| 5,299,284 A * | | 3/1994 | Roy ............................... 706/20 |
| 5,311,876 A | | 5/1994 | Olsen et al. ................... 128/731 |
| 5,465,321 A * | | 11/1995 | Smyth ............................ 706/20 |
| 6,171,256 B1 * | | 1/2001 | Joo et al. ....................... 600/508 |
| 6,217,525 B1 * | | 4/2001 | Medema et al. .............. 600/508 |
| 6,487,310 B1 * | | 11/2002 | Bishop et al. ................. 382/186 |
| 6,572,542 B1 | | 6/2003 | Houben et al. ................ 600/300 |
| 6,675,159 B1 * | | 1/2004 | Lin et al. ......................... 1/1 |
| 6,923,763 B1 * | | 8/2005 | Kovatchev et al. ........... 600/300 |
| 7,314,451 B2 * | | 1/2008 | Halperin et al. .............. 600/534 |
| 7,496,210 B2 * | | 2/2009 | Shi et al. ....................... 382/100 |
| 2002/0138492 A1 * | | 9/2002 | Kil ................................. 707/100 |
| 2003/0195429 A1 | | 10/2003 | Wilson .......................... 600/544 |
| 2004/0167580 A1 * | | 8/2004 | Mann et al. .................... 607/17 |
| 2004/0267152 A1 | | 12/2004 | Pineda .......................... 600/544 |
| 2005/0240544 A1 * | | 10/2005 | Kil et al. ....................... 706/45 |
| 2006/0111933 A1 * | | 5/2006 | Wheeler ......................... 705/2 |
| 2007/0015971 A1 * | | 1/2007 | Atignal et al. ................ 600/300 |
| 2008/0015447 A1 * | | 1/2008 | Towler et al. ................. 600/477 |
| 2008/0208072 A1 * | | 8/2008 | Fadem et al. ................. 600/544 |
| 2008/0301077 A1 * | | 12/2008 | Fung et al. ..................... 706/46 |
| 2008/0306353 A1 * | | 12/2008 | Douglas et al. ............... 600/301 |
| 2011/0274361 A1 * | | 11/2011 | Bovik et al. .................. 382/224 |

FOREIGN PATENT DOCUMENTS

| | | |
|---|---|---|
| EP | 0699413 A1 | 3/1996 |
| WO | WO 02/069798 A1 | 9/2002 |
| WO | WO 2005/037092 A2 | 4/2005 |

OTHER PUBLICATIONS

Dasarathy B., SPIE Conf. on Automatic Target Recognition VIII. SPIE vol. 3371 : 356 (Apr. 1998).*
Jain et al., Statistical Pattern Recognition: A Review. IEEE Tran. on Pattern Analysis and Machine Intelligence, vol. 22, No. 1, Jan. 2000.*
An Itroduction to EEG Brain Imaging Workshop Dec. 2002 http://psyphz.psych.wisc.edu/~greischar/BIW12-11-02/EEGintro.htm.*
Shimozaki et al. J. of Vision 3 : 209 (2003).*
Thomaz et al., IEEE Transactions on circuits and systems for Video Technology 14 (2) : 214 (2004).*
Williams et al. IEEE Transactions on Pattern Analysis and Machine Intelligence 20 (12) : 1342 (1998).*
Bjørgaas, M., et al., "*Quantitative EEG During Controlled Hypoglycaemia in Diabetic and Non-Diabetic Children,*" Diabetic Medicine, 1998, vol. 15: 30-37.
Ebersole, John S., M.D., et al., "*Current Practice of Clinical Electroencephalography,*" Lippincott Williams & Wilkins, 3d, pub. Chpt. 4, pp. 72-74, 2003.
Gade, J., et al., "*Detection of EEG Patterns Related to Nocturnal Hypoglycemia,*" Meth Inform Med 1994; 33: 153-6.
Jasper, Herbert H., M.D., "*Report of the Committee on Methods of Clinical Examination in Electroencephalography,*" vol. 10, No. 2, 1958, pp. 370-375.
Rowan, A. James, M.D., et al., "*Primer of EEG With a Mini-Atlas,*" Butterworth Heinemann Chpt. 1, 2003.
Tavakolian, Kouhyar, "*Mental Task Classification for Brain Computer Interface Applications,*" CSCBC, First Canadian Student Conference on Biomedical Computing pp. 1-6, (2006).
Tupola, Sarimari, M.D. et al., "*Abnormal Electroencephalogram at Diagnosis of Insulin-Dependent Diabetes Mellitus May Predict Severe Symptoms of Hypoglycemia in Children,*" The Journal of Pediatrics, vol. 133, No. 6, Dec. 1998, pp. 792-794.
Zeitlhofer, Josef, M.D., Ph.D., "*EEG Topography During Insulin-Induced Hypoglycemia in Patients with Insulin-Dependent Diabetes Mellitus,*" Eur Neurol 1996; 36:303-309.

* cited by examiner

*Primary Examiner* — Ethan Whisenant
(74) *Attorney, Agent, or Firm* — O'Keefe, Egan, Peterman & Enders LLP (57) ABSTRACT

Features indicative of hypoglycaemia in EEG signals are detected by: —dividing EEG signals into a sequence of time segments, —for each time segment determining whether a pattern of EEG signals is present which is indicative of hypoglycaemia and, where a pattern of EEG signals indicative of hypoglycaemia is determined to be present in a time segment, recording this as an event, —integrating the number of events recorded during a selected number of preceding time segments which together constitute a selected time period, optionally in a time weighted manner, and—determining that the EEG signals are indicative that hypoglycaemia is present based on said integration when the said integrated number of events exceeds a preset threshold number and/or when there exists a threshold level of matching between a curve of said integration over time and a previously established ideal model of said curve indicative of hypoglycaemia.

21 Claims, 6 Drawing Sheets

ANALYSIS OF EEG SIGNALS TO DETECT HYPOGLYCAEMIA

The invention relates to a method of predicting and warning of hypoglycaemic attacks for people such as but not limited to diabetics. Moreover the invention relates a device for prediction and warning of hypoglycaemic attacks for people such as but not limited to diabetics.

Hypoglycaemic attacks occur as a result of a too low blood sugar concentration, which is mostly a problem for diabetics, who are treated with insulin or other blood sugar regulating medical drugs. Others at risk include those having a genetic predisposition to having a low blood sugar. The attacks can be highly severe and often entail unconsciousness. The risk of an attack therefore often limits the possible activities of the people concerned, which furthermore decreases their quality of life. Attacks can be prevented in a simple way, e.g. by consuming appropriate food when glucose values become critical. The problem is however that many in the risk group cannot by themselves sense when their blood sugar concentration reaches a critically low level with risk of an attack. The number of people in the risk group is approximately 10 million.

There are known methods and devices for prediction of hypoglycaemic attacks.

In U.S. Pat. No. 6,572,542 a method and a device are described, which among others have the purpose of warning of hypoglycaemic attacks. This uses a combination of EEG measurements to indicate an individual's blood glucose level and the individual's ECG (electrocardiographic) signals to indicate the rate of change of blood sugar concentration as inputs to an artificial neural network learning processor, from which is obtained a signal that is used for alerting the user or to control administration of a therapeutic material.

However, no specific method of obtaining or analysing EEG signals is described and nor are any results of practising the described methods given.

Gade J., Rosenfalck A. and Bendtson I., Meth Inform Med 1994; 33: 153-6 investigates the possibility of providing a patient hypoglycaemia alarm and describes the detection of EEG patterns related to nocturnal hypoglycaemia. EEG signals from bipolar EEG surface electrodes C4-A1 and C3-A2 are digitised offline and are divided into 2 second time segments. Amplitude and spectral content from these is fed to a Bayes probabilistic classifier of undisclosed type which is trained according to an unsupervised learning process. The rate of occurrence of events classified as indicative of hypoglycaemia is observed. It is concluded that inter-patient variability does not allow for the construction of a common learning set for all patients and that construction of a personal learning set will be required for all patients.

We have now found that in order to obtain sufficient specificity and sensitivity of detection of EEG changes indicative of the onset of hypoglycaemia, it is not sufficient to consider only the occurrence of such changes nor the rate at which they occur. Otherwise, sporadic EEG events consistent with hypoglycaemia or temporary bursts of such events can lead to a false alarm being triggered.

Accordingly, the present invention now provides a method for the analysis of EEG signals to detect features therein which are indicative of hypoglycaemia comprising:

dividing EEG signals into a sequence of time segments,
for each time segment determining whether a pattern of EEG signals is present which is indicative of hypoglycaemia and, where a pattern of EEG signals indicative of hypoglycaemia is determined to be present in a time segment, recording this as an event,
integrating the number of events recorded during a selected number of preceding time segments which together constitute a selected time period, and
determining that the EEG signals are indicative that hypoglycaemia is present based on said integration, for instance, when the said integrated number of events exceeds a preset threshold number and/or when there exists a threshold level of matching between a curve of said integration over time and a previously established ideal model of said curve indicative of hypoglycaemia. Basing the determination on the integration avoids false positive results due to sporadic time segments containing events or sporadic clusters of such time segments. The determination is therefore made when a characteristic rising incidence of such events occurs.

Preferably, said integration is performed as a weighted integration in which events detected in time segments further back in time are given a lesser weighting than events detected in more recent time segments. Such a weighted integration may be performed using a linear weighting function or a sine-curve weighting function or other weighting functions.

Preferably, determination of whether a pattern of EEG signals is present in a time segment which is indicative of hypoglycaemia is performed by applying to said signals a previously trained Bayes classifier, a support vector machine (SVM), a relevance vector machine (RVM), a Gaussian process classifier, a classifier based on Fisher's discriminant, a boosted classifier, a naïve Bayes classifier, a K-nearest neighbour classifier, a Binary Decision Tree, a Parzen Window classifier, or a neural network. A suitable Bayes classifier may be a Bayes Gaussian classifier.

Optionally, during a period of monitoring EEG signals there is carried out a re-estimation of the mean and covariance parameters of the Gaussian model over time. This may be used to compensate for drift in these parameters.

Preferably, said classifier is a quadratic Bayes Gaussian classifier.

The previously trained classifier applied to said signals is preferably a classifier trained by supervised learning, however an unsupervised learning trained classifier may be employed. A supervised Bayes classifier may use a Gaussian PDF (probability density function) as a model or a mixture of Gaussian PDF's as a model.

The raw EEG signals are preferably subjected to spectrum analysis to extract therefrom power averages in at least four frequency bands upon which is based the said determination of whether a pattern of EEG signals is present which is indicative of hypoglycaemia in a time segment of said signals. The at least five frequency bands preferably cover frequencies from 2 Hz to 32 Hz and suitable values for the bands include bands of approximately (2 Hz-5 Hz), (5 Hz-8 Hz), (8 Hz-11 Hz), (11 Hz-14 Hz) and (14 Hz-32 Hz), wherein all of the boundaries of said frequency bands are variable by up to 20%. The ideal number of bands and their respective coverage may vary from person to person and may be optimised for an individual.

Prior to said spectrum analysis, artefact or noise elements in said EEG signals are preferably identified and eliminated.

The EEG signals may be obtained from electrodes applied to the surface of the scalp, but in order to reduce noise and to obtain a more consistent output, the use of subcutaneously implanted electrodes is preferred. Electrodes may additionally or alternatively be inserted into the brain itself. The position of these will affect the content of the signals that is modulated by glycaemic status and also the amount of noise due to non-relevant signal generators such as motor activity.

Figure 2:
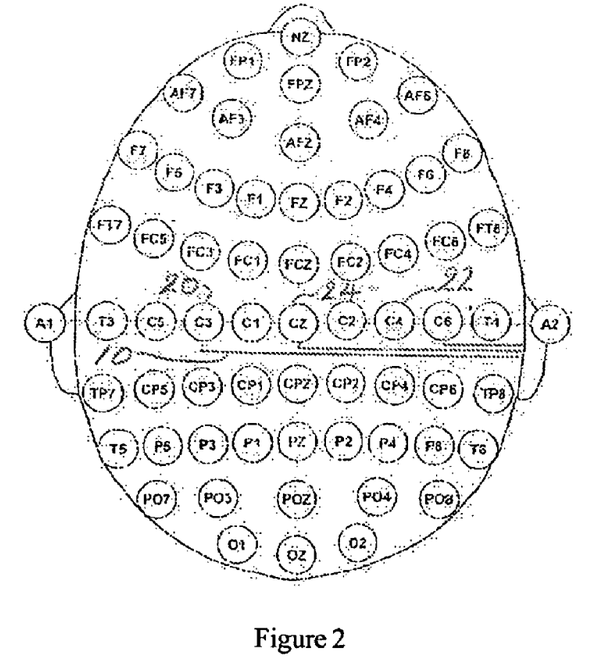
FIG. 2 shows the electrode array of the apparatus of FIG. 1 seen from above superimposed on a standard map of EEG electrode positions.

Preferably, said EEG signals are obtained from one or more electrodes positioned within the area bounded by the FC3-FC1-C1-CP1-P1-PO3-P5-CP5-C5 standard EEG electrode positions and/or in an equivalent area around C4. Reference may be made to FIG. 2 for an illustration of these positions.

More preferably, the electrodes are positioned within the area bounded by the FC3-FC1-C1-CP1-CP3-C5 positions and/or in the equivalent area around C4 and still more preferably within the area bounded by the FC3-C1-CP3-C5 positions and/or in the equivalent area around C4.

Thus, most preferably said EEG signals have been obtained from one or more electrodes positioned in at least approximately the C3 and/or C4, but electrodes at the P3 and/or P4 standard EEG electrode positions would be acceptable.

Preferably, said signals are measured with reference to signals obtained from a reference electrode positioned approximately on the frontal-occipital mid-line, e.g. in approximately the Cz or Pz standard EEG electrode position.

Optionally, one derives signals from a number of electrodes (suitably up to five) along the "line" T3, C5, C3, C1, Cz, C2, C4, C6, T4 or the line TP7, CP5, CP3, CP1, CPz, CP2, CP4, CP6, TP8 or the line T5, P5, P3, P1, Pz, P2, P4, P6, T6. Using more than two differential electrodes allows to use techniques such as Independent Component Analysis (ICA) to find artefact noise, and remove this noise from the EEG signals as discussed further below. The use of multiple electrode positions spaced along a straight or curved line facilitates the use of implanted electrodes as the conductors connecting thereto can all be led out in the same direction along a common path.

Preferably, the time period is adjusted to optimise the sensitivity and specificity of the determination that the obtained signals are indicative of hypoglycaemia for an individual from whom the signals originate. A similar individual optimisation may be carried out by adjustment also of the duration of the time segment or of the overlap of one time segment with the next, which may for instance be within the range of 0 to 50%. Time segments may also be spaced from each other with signals in between time segments being ignored.

EEG signals are optionally determined to be indicative of hypoglycaemia by establishing that a threshold level of matching between the curve of said integration over time and a previously established ideal model of said curve indicative of hypoglycaemia exists, wherein said matching is carried out by a mathematical convolution of the measured and ideal curves. Alternative pattern matching techniques are discussed below. The ideal curve used as the basis for the comparison may be a generic one applied to all users or may be individually determined based on observation of the shape of curve characteristic of a hypoglycaemic attack in that particular user.

In the methods exemplified below, each time segment is considered to contain an event characteristic of hypoglycaemia on the basis of features constituted by the power averages of each of the (typically five) frequency bands in that time segment for each electrode. These are the features operated on by the classifiers discussed. Whilst this has been found to be adequate, alternative methods may prove more robust to noise in the system. These may include splitting the signal into frequency bands by the use of filters matched to the characteristic form of the EEG signals in a hypoglycaemia event. Alternatively, one may use features found by mathematically convolving the actual EEG signal during the time period with and ideal form for the EEG signal in a hypoglycaemic episode. Alternatively, use can be made of features found from wavelet transformation of the measured curve or from singular value decomposition, or of features found by Independent Component Analysis or from a non-zero matrix factorisation (NMF) or other matrix factorisation or decomposition technique.

The method preferably includes activating an alarm upon determination that the EEG signals are indicative of hypoglycaemia. The alarm may take any form suitable to alert the user or a carer. In particular, it may be audible, visible, a mild electric shock, and/or a vibration alarm.

The invention includes apparatus for use in a method as described and comprising pre-programmed computation means comprising inputs for receiving EEG signals from EEG electrodes, and means for     dividing said EEG signals into a sequence of time segments,     for each time segment determining whether a pattern of EEG signals is present which is indicative of hypoglycaemia and, where a pattern of EEG signals indicative of hypoglycaemia is determined to be present in a time segment, recording this as an event,     integrating the number of events recorded during a selected number of preceding time segments which together constitute a selected time period,     determining that the EEG signals are indicative that hypoglycaemia is present based upon said integration, and     providing an output indicating that said threshold number has been exceeded.

Said output preferably takes the form of an alarm as described above.

The apparatus may comprise one or more electrodes for positioning on a user, or actually in position on a user, from which to obtain such EEG signals.

The conditions for triggering the giving of an alarm may be differently set according to whether the user is going to be awake or asleep during the period of monitoring. EEG signals from an awake user on the one hand and EEG signals from a sleeping user on the other each present different complicating factors in distinguishing the EEG changes associated with hypoglycaemia from other features of the EEG. Thus, EEG signals from an awake user are likely to be contaminated with a higher level of artefact signals relating to motor functions. On the other hand, when the user is asleep, changes in the EEG caused by sleep will to some degree mimic the changes which would be due to hypoglycaemia, making the task of distinguishing the EEG changes due to hypoglycaemia more difficult. Thus, the awake/asleep status of the user may be used as an input to the computation in the device so as to have an effect on the threshold levels of the integration or the degree of matching of the integration curve to an ideal curve (or the shape of the ideal curve).

Other factors may also be included in determining the threshold levels of the integration or the degree of matching of the integration curve to an ideal curve (or the shape of the ideal curve). These may include, the time of day, the heart rate, the temperature as measured at the skin surface and other relevant inputs. However, it is preferred that ECG signals are not used as inputs to the apparatus or in the method of the invention. The determination of a hypoglycaemic condition will ordinarily be based exclusively on the EEG signals.

As a further aid to determining when hypoglycaemia is beginning, the integration threshold method describe above may be supplemented by matching the measured shape of the integration curve to a previously established characteristic ideal shape for the curve, which is indicative of hypoglycaemia. Such matching to the ideal curve may be carried out as a mathematical convolution of the measured curve with the ideal curve, or by template matching, or cross-correlation. Thus, for hypoglycaemia to be determined to be present and for an alarm signal to be triggered it may be required that the integration threshold should be reached or that a sufficient degree of match should exist between the integration curve and an ideal curve, or both. The invention includes a method of monitoring the glycaemic status of a user comprising, attaching or implanting electrodes to gather EEG signals containing information relating to glycaemic status, acquiring said EEG signals, and subjecting said signals to a method of analysis as described above.

The invention will be further illustrated and explained by the following description of preferred embodiments with reference to the accompanying drawings, in which.

Figure 1:
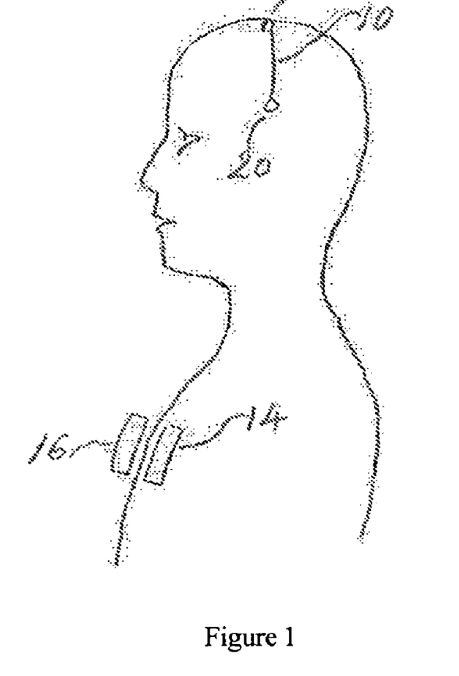
FIG. 1 shows schematically a person equipped with an example of apparatus according to the invention for detecting the onset of hypoglycaemia.

As shown in FIG. 1, apparatus according to the invention may comprise an array of subcutaneous EEG electrodes 20, 22 (FIG. 2) and 24, connected by implanted electrical connection wires 10 to an implanted signal processing/transmitting unit 14 positioned adjacent an externally worn signal processing/alarm unit 16.

Power may be provided from unit 16 to unit 14, for instance by magnetic induction, and unit 16 itself may be powered by conventional rechargeable batteries.

The array of electrodes 10 may comprise any desired number of electrodes. Also, although the illustrated apparatus uses implanted subcutaneous electrodes, skin surface electrodes may alternatively be used, or a combination of external and subcutaneously or intracranially implanted electrodes may be used. For convenience, it is desirable to reduce the number of electrodes to the minimum consistent with producing reliable results. Preferably therefore, as illustrated, the array consists of three electrodes arranged along a path defined by a set of electrical conductors which run parallel and closely adjacent to one another as seen in FIG. 2. Here, two signal electrodes 20 and 22 are positioned in approximately the C3 and C4 positions respectively and a reference electrode 24 is positioned in the Cz position, referring here to the standard International 10-20 position mapping for EEG electrodes as described for instance in 'Primer of EEG with a Mini-Atlas', Rowan and Tolunsky (Butterworth Heinemann) Chapter 1, FIGS. 1-1 to 1-6, or the extended 10-20 system as described in 'Current Practice of Clinical Electroencephalography' third edition, Ebersole and Pedley Ed, Lippincott, Williams & Wilkiks pub, Chapter 4, pages 72-74.

Whilst these positions are favoured, they are not critical and may be varied. For instance, any position within the area bounded by the FC3-FC1-C1-CP1-P1-PO3-P5-CP5-C5 positions (and similarly around C4), e.g. within the area bounded by FC3-FC1-C1-CP1-CP3-C5 positions (and similarly around C4) would be acceptable with in the preferred practice of the invention, especially in the area bounded by FC3-C1-CP3-C5 (and similarly around C4). Suitably alternative specific electrode positions would be P3 and P4. For the reference electrode, any position between Fz and POz would be preferred, especially between FCz and Pz.

As described in detail below, considerable amplification and computer processing of the raw EEG signals derived from the electrodes is necessary in the methods and apparatus of the invention. This may be conducted either in the implanted unit 14 or in the externally worn unit 16 or may be split between the units in any desired manner.

Amplification of the EEG electrode signals may be performed in a standard manner, e.g. by op-amp instrumentation amplifiers. The signals may be converted from analogue to digital in a known manner for further processing and analysis. The digitised signals may be segmented into time segments or epochs, suitably of from 0.5 to 2 seconds, one second being preferred. As explained above, the time segments may overlap so that data from the end of one time period is re-used in the next, or may be spaced leaving some data out. In the preferred apparatus, the 1 second time segments are sub-sampled to a frequency of 64 Hz. Each segment consists of data from two differentially recorded channels (C4-Cz) and (C3-Cz), giving 128 bits of data in each segment.

The apparatus contains, either in the unit 14, or in the unit 16, or split between them, computation means for carrying out the following operations.

Artefact Removal

The raw EEG signals contain signal elements deriving from brain activity modulated by glycaemic status but also noise or artefact signal elements relating to irrelevant matters, especially body movements, including eye movements. In one approach, time segments containing excessive noise/artefact signals are rejected prior to further signal analysis. In another approach, the data within time segments is corrected to exclude the artefact signals without losing the relevant signals. One may include either or both of these approaches in the handling of the signals.

Various methods may be employed for artefact removal. In one preferred method, the variance or sample variance of the signal (maximum value of the mean power for each EEG channel) in each time segment is evaluated. Time segments with a variance above a threshold level are rejected. The threshold may be set such that about 10% or 20% of the data is rejected.

A more subtle alternative which may be employed additionally to or instead of the above approach is to apply an algorithm to the EEG signals to identify artefact signal patterns and to remove them more specifically. An example of such an algorithm follows that operates unsupervised and bases its whole analysis on the EEG signal itself. This kind of algorithm is mostly referred to as blind-source-separation (BSS) and independent-component-analysis (ICA). These algorithms have previously been used when analyzing EEG signals, to find EEG sources in the brain, but are not known to have been used previously for cleaning signals relating to hypoglycemia. ICA works well when there are many input dimensions (here EEG electrode signals), but not as well when using fewer electrodes. Accordingly, this approach will be favoured when more than just the C3 and C4 electrodes referred to above are employed. For instance, more electrodes may be provided on or close to the line from C3 to C4. An alternative approach where the number of electrodes is low (e.g. just C4, Cz, and C3) would be to use "sparse regression", a technique that assumes that there exists an underlying subspace of signal components that are used sparsely. Sparse regression is also sometimes referred to as: basis pursuit, atomic decomposition, and Sparse Component Analysis.

Figure 3:
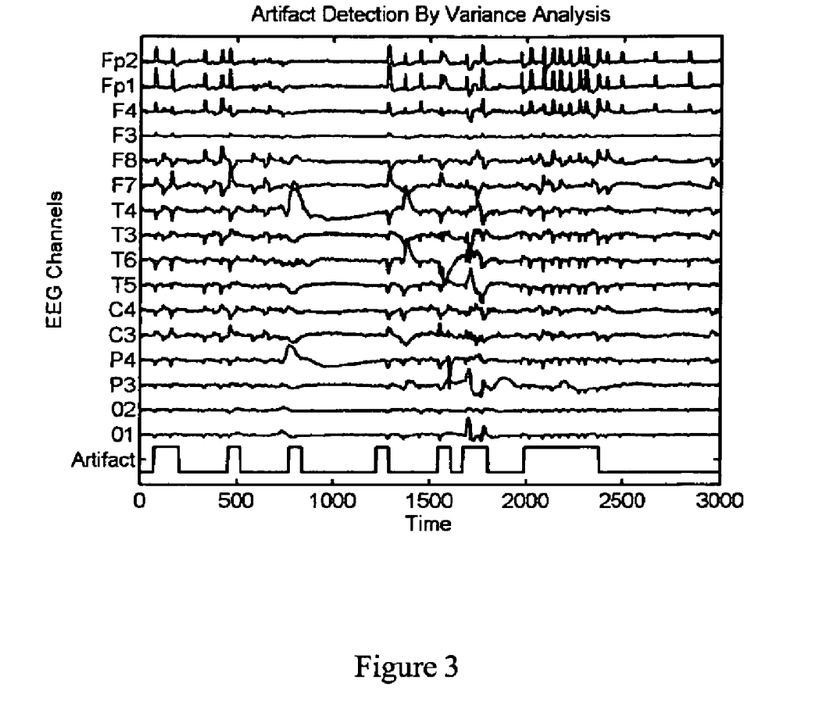
FIG. 3 shows signals from 16 EEG channels marked with artefacts (lowest trace) identified by calculation of signal variance.

One option is to provide further electrodes for signal gathering, to employ ICA to identify and remove artefacts and then to base the detection of hypoglycaemia on the cleaned signals from a more limited set of the electrodes such as just C3, C4 and Cz. An example of this will be illustrated. FIG. 3 shows EEG signals from 16 channels over 3000 seconds subjected to variance analysis to identify periods containing artefacts, mainly associated with eye movement. The bottom signal (Artefact) shows the time segments where artefacts are detected due to the high EEG signal variance. These parts of the EEG signal, constituting in this instance 20%, are removed. These large artefacts may be associated with major motor activity such as jaw movements. The 20% of the EEG signals that have been removed are determined by analysis of the EEG signal power histogram using a reject fraction of 0.2.

Figure 4:
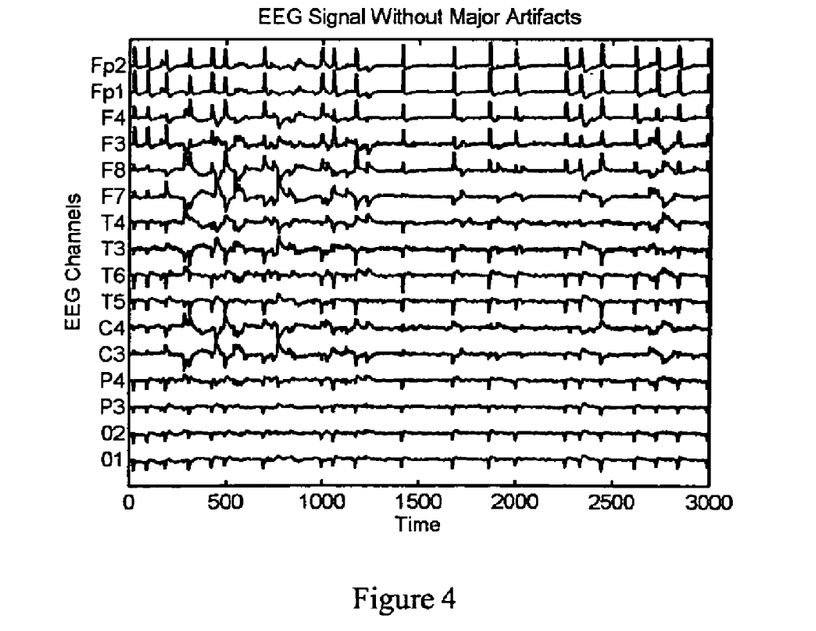
FIG. 4 shows the same signals after removal of the major artefacts.

The remaining signals after removal of the artefacts identified in FIG. 3 are shown in FIG. 4. However, the signals are still contaminated to a degree with artefacts mainly related to more minor motor activity such as eye movements and these are further reduced by the use of ICA.

Figure 5:
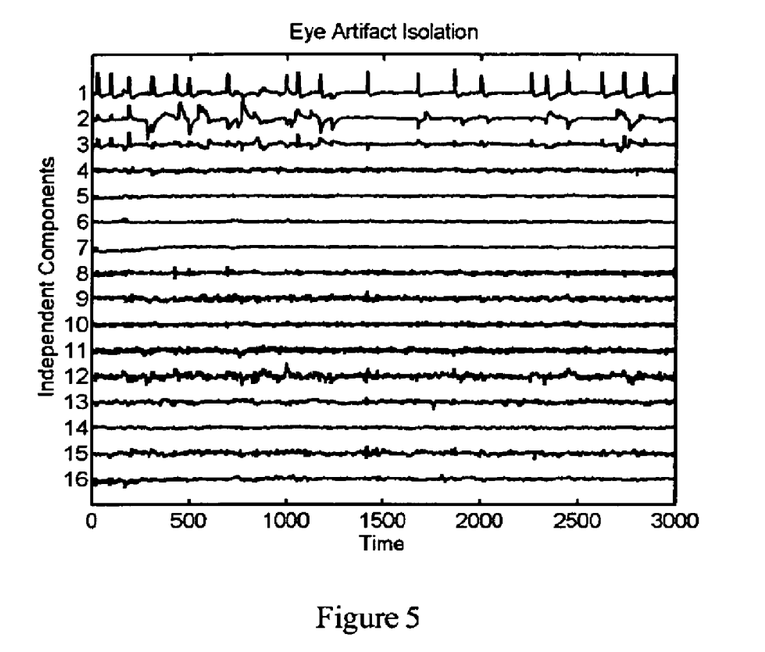
FIG. 5 shows the result of Independent Component Analysis (ICA) performed on 16 channels of EEG signals following major artefact removal.
Figure 6:
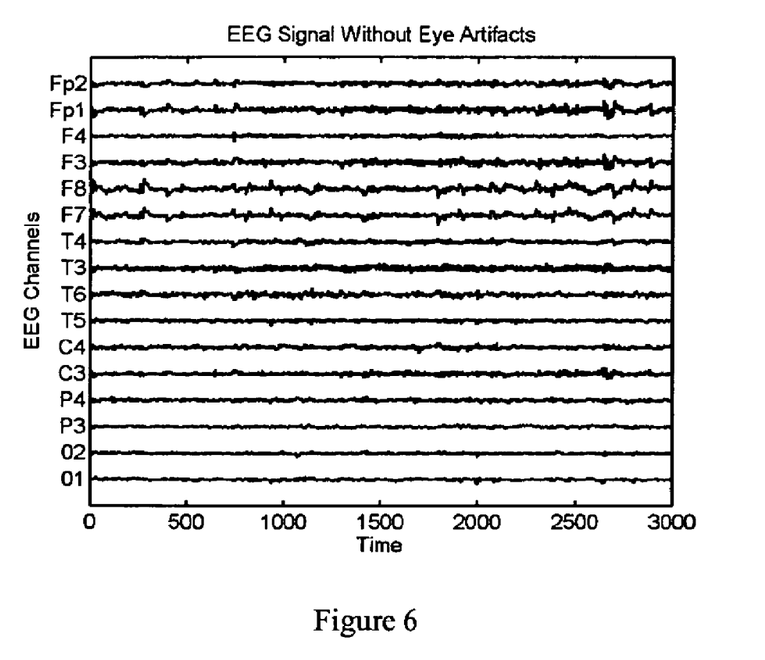
FIG. 6 shows EEG signals further cleaned of artefacts identified by ICA.

The artefact parts originating from subject eye movement are determined in this case by the use of a maximum likelihood independent component analysis (ICA) algorithm. The ICA algorithm finds 16 independent signal components from the 16 EEG signals. Three of these independent signal components are directly related to eye movement. The three components are removed by subtracting them from the original EEG signal, whereby none of the remaining EEG time slices are removed. FIG. 5 shows the 16 independent components found in the EEG signals. The first three independent components are here directly related to eye movement. Components related to eye movement can be identified by consideration of the extent to which they appear in signals from frontal electrodes or by comparing signals obtained when the subject is asked to make a lot of eye movements or to blink frequently. After removing the three most active eye movement components, the EEG signals are sufficiently cleaned from artefacts, for the machine learning algorithms to be applied as described in the next section. FIG. 6 shows the cleaned EEG signals. Traces from eye movement artefacts can still be spotted, but the signal is sufficiently clean for the machine learning algorithms to be applied.

Feature Extraction

Following artefact removal, it is desirable to extract the information that is contained in separate frequency bands within the overall signals. We have found that it is preferable to use as many as five bands, each of 3 Hz in width, as follows: 2-5 Hz, 5-8 Hz, 8-11 Hz, 11-14 Hz and 14 Hz-32 Hz.

Many other patterns of band division can be used of course. The general pattern observed in an EEG upon the onset of hypoglycaemia is an increase in the power present in the delta band (1-4 Hz) but more especially in the theta band (4-8 Hz) and a lowering of the frequency of the component in the alpha band (8-12 Hz) at which most power is present. These effects are particularly noticeable in EEG signals from the C3 and C4 regions.

Previous work has often concentrated exclusively on the information in the theta and alpha wave bands, but we have found it much better to sub-divide the frequencies in a finer manner. Also, better results are obtained by leaving out frequencies below 2 Hz. However, an alternative division of the frequencies with which we have produced good results is 0.8 Hz-1.3 Hz, 1.3 Hz-2.2 Hz, 2.2 Hz-3.6 Hz, 3.6-5.9 Hz, 5.9 Hz-9.5 Hz, 9.5 Hz-15.6 Hz, 15.6 Hz-25.6 Hz and 25.6 Hz-32 Hz. Good results can also be achieved at least in some cases by using fewer bands, e.g. 3.6-5.9 Hz and 5.9-9.8 Hz. The limits of each band indicated above are only exemplary and can freely be changed, e.g. by ±10% to 20%.

The above described division of the signals into from 5 to 8 frequency bins in each of the two channels C3-Cz and C4-Cz enhances the classification results obtained in the next stage when compared to the traditional division of frequencies into alpha, beta, theta and delta bands. However, using only two bands can result in a model that is so general that it can be used as an inter-subject model, rather than requiring the training of a model for each individual. One can use fewer bands and a more generally applicable model for more 'typical' individuals and use more bands and an individually trained model for users who do not suit the general model.

One can also include in the data the value of the frequency in the range 2-12 Hz at which maximal power is contained, as this we have found to decrease during hypoglycaemia.

Event Detection

We shall describe the extraction from the frequency filtered signals of events signalling hypoglycaemia using in one case a quadratic Bayes Gaussian Classifier (QBGC) and in the other case a neural network. It will be appreciated that one may classify the information in the time sliced, frequency divided signals using many other classifiers of known types as described above.

Software for carrying out classification to identify relevant events may be obtained from a number of sources, for instance http://www.ll.mit.edu/IST/lnknet/.

In our QGBC, The classification of the EEG signals is partly based on the quadratic measure shown in Equation 1, which defines the Bayesian normal distributed classifier, with a diagonal covariance matrix, a simplification of the full quadratic classifier. It should be noted that all the parameters in the equation are vectors.

$$\text{Quadratic Measure} = \frac{(x - \mu_{pos})^2}{\sigma_{pos}^2} - \frac{(x - \mu_{neu})^2}{\sigma_{neu}^2}$$

This Quadratic Measure is used for simple discrimination between hypoglycaemic and neutral events. Each 1 second of data (or other selected length of time segment or epoch) is classified in a binary manner as either hypoglycaemic or neutral. The neutral events are when the signals indicative of an hypoglycaemic event are not present. The variables (x, μ and σ) all are vectors of dimension (channels×features per channel). The 'features' here are the total or average power within each band in each time segment for each channel.

In the quadratic measure, all the features in the channels are all contributing equally to the measure. The good and bad (relevant and irrelevant) features are therefore represented equally when using the quadratic measure for classification. To get a better weighting of the features, we can instead use a neural network based measure, where the features are weighted according to their ability to discriminate between the hypoglycaemic and neutral events. A neural network classifier finds the best combination of the inputs, where the quadratic classifier used an averaged combination of the inputs.

An example of a suitable artificial neural network is one that is a regularized two layer feed-forward neural network with a hyperbolic tangent function for the hidden layer and a logistic sigmoid function for the output layer. The weights may be optimized using the cross-entropy error function augmented with a Gaussian prior over the weights. Suitably this may be a 7-10 hidden units network. More hidden units can result in overtraining and less units may give to little flexibility. The optimal number of hidden units is dependent on the amount of training data, meaning that using slightly more units might give better results if more training examples are available.

The Bayes classifier or the neural network is trained using supervised learning. Events indicative of hypoglycaemia are manually marked in signals obtained from an individual. The markings are done by experts in the use of EEG who visually detect what they consider to be relevant EEG signal patterns. Some hundreds of time segments of data are used for training and within these there must be at least one representing a hypoglycaemic event.

The trained classifier is then used in real time to classify the digitised, cleaned and feature extracted signals from the EEG electrodes.

Determination of the Onset of Hypoglycaemia

At intervals, events will occur that are classified as hypoglycaemic amongst a stream of events classified as neutral. In order to form a sound basis for judging that a real hypoglycaemic condition is developing however, with adequate specificity and sensitivity, it is not sufficient to rely on the occurrence of one such classified event nor even to determine when the rate at which such events occur exceeds some threshold level. Such events may be detected sporadically and may come in clusters at a high rate for a period, even when no actual hypoglycaemic condition exists.

Accordingly, according to the invention, the apparatus integrates the detected events over a selected time period. Events cease to be counted in the integration when a sufficient time has passed since they occurred. According to a preferred practice of the invention, as events recede in time, they are given a decreasing weighting in the integration. Suitably the weighting may be according to a sine function, e.g. according to the equation:

$$\text{Weight} = \sin\left(\frac{\pi \times T_d}{600}\right)$$

where $T_d$ is the time in seconds since the classified hypoglycaemic event happened, where only events within the last 300 seconds are considered. More generally, '600' is replaced by $2 \times T_p$ where $T_p$ is the selected time period.

Alternatively, a linear weighting reducing from one to zero over $T_p$ may be employed.

These schemes treat events classified as hypoglycaemic as being of more predictive value if they are recent than if they happened some time ago.

A more complex weighting scheme may be employed in which the weighting given to events further in the past is decreased if the rate of events occurring at that time is higher. For instance, an event that occurred three minutes ago could be given a weighting of 1.0 if up to that time the integrated number of events is only 1, but a decreased weighting on a continuous sliding scale if the integrated number of events up to then is higher, for instance a weighting of 0.66 if the integrated number of events up to then is 2 and 0.5 if the integrated number of events up to then is 3. This will lead to a penalisation of the integration function when events do not follow the pattern that genuinely signals hypoglycaemia, where the rate of occurrence of events characteristically increases in a roughly exponential manner.

Figure 7:
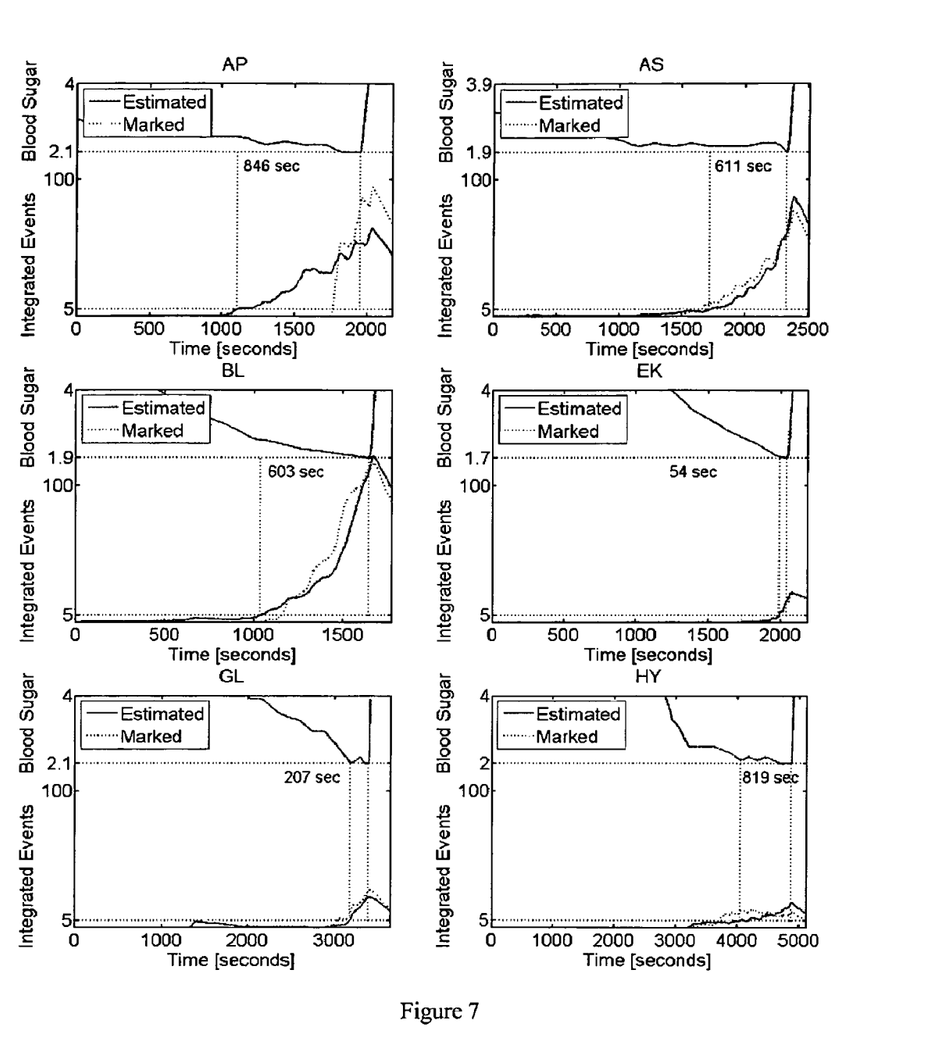
FIG. 7 shows results of the analysis of EEG signals from six individual volunteers in which events relevant to the occurrence of hypoglycaemia have been identified and integrated over a selected time period.
Figure 8:
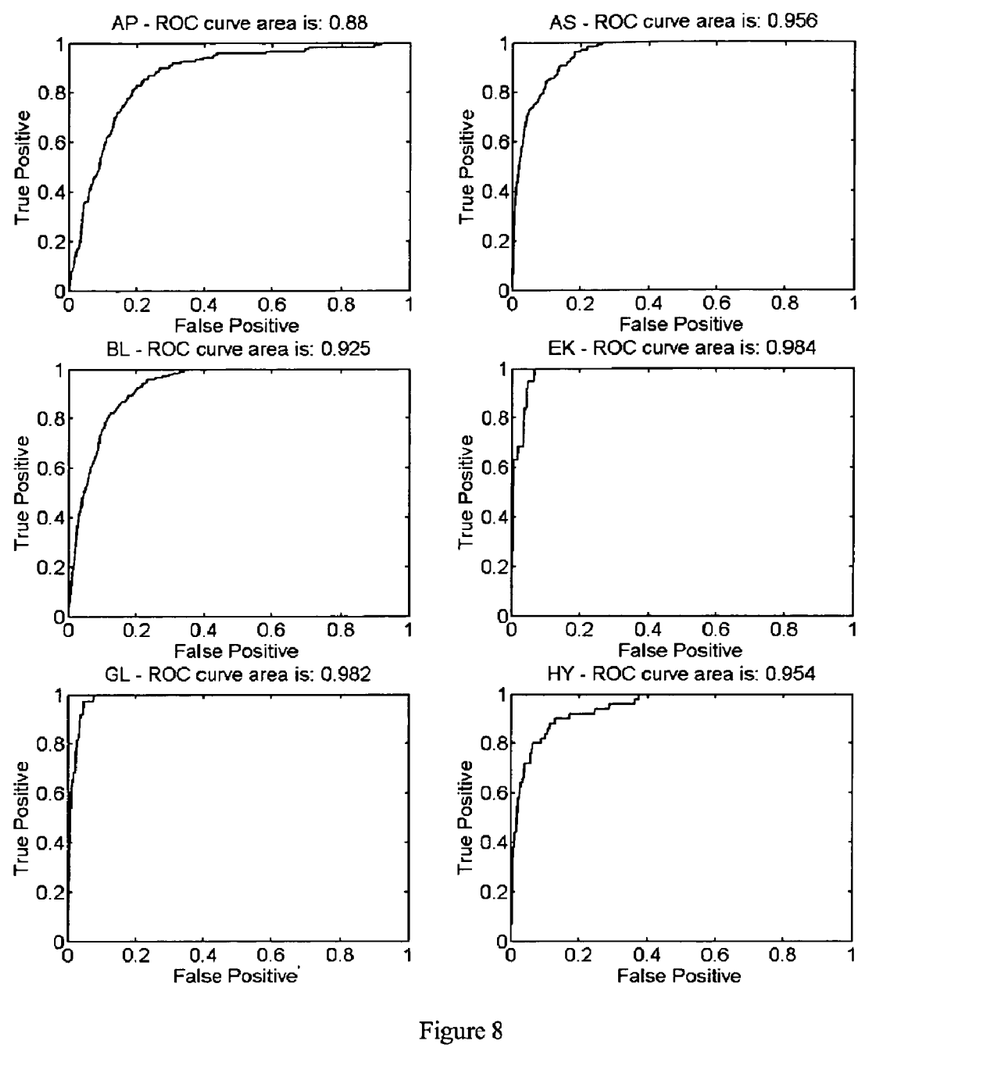
FIG. 8 shows ROC curves for each volunteer based on the signal analysis for which results are shown in FIG. 7.

Examples of the effect of the use of the QBGC and the integration of events are seen in FIGS. 7 and 8. FIG. 7 shows results obtained for six individuals identified by anonymised initials AP, AS, BL, EK, GL and HY. Data was gathered for each volunteer over a period during which the blood glucose level was caused to fall. Blood glucose measurements are plotted in the upper panel of each volunteer's results. Here, in a simulation of the operation of the invention, the classifier for each individual has been trained on one half of the available data divided into non-overlapping 1 second time segments for four 3 Hz wide bands from 2 Hz upwards plus a 14 Hz-32 Hz band and has then been used to classify the remaining half of the data offline.

Integration curves are plotted of events within a 600 second time period using the sine weighting described above. The effect of setting a 5 event threshold is indicated. Due to the weighting process, the threshold could of course be set to a non-integral value. The solid curves show the output of the classifier and the dotted integration curves show results based on manual marking.

In FIG. 8 are shown ROC curves for each volunteer. A high figure (close to 1.0) for the area under the curve indicates a better result, 0.5 being effectively the worst possible outcome.

It can be seen that for each volunteer the general shape of the integration curve is similar. Hypoglycaemia is indicated by a rising frequency of the occurrence of events giving rise to integration curves that rise in a roughly exponential manner. The threshold value of 5 events is crossed in time for an alarm given at that point to allow a user sufficient time to take action to raise the blood sugar before hypoglycaemia renders them not competent to do so.

Figure 9:
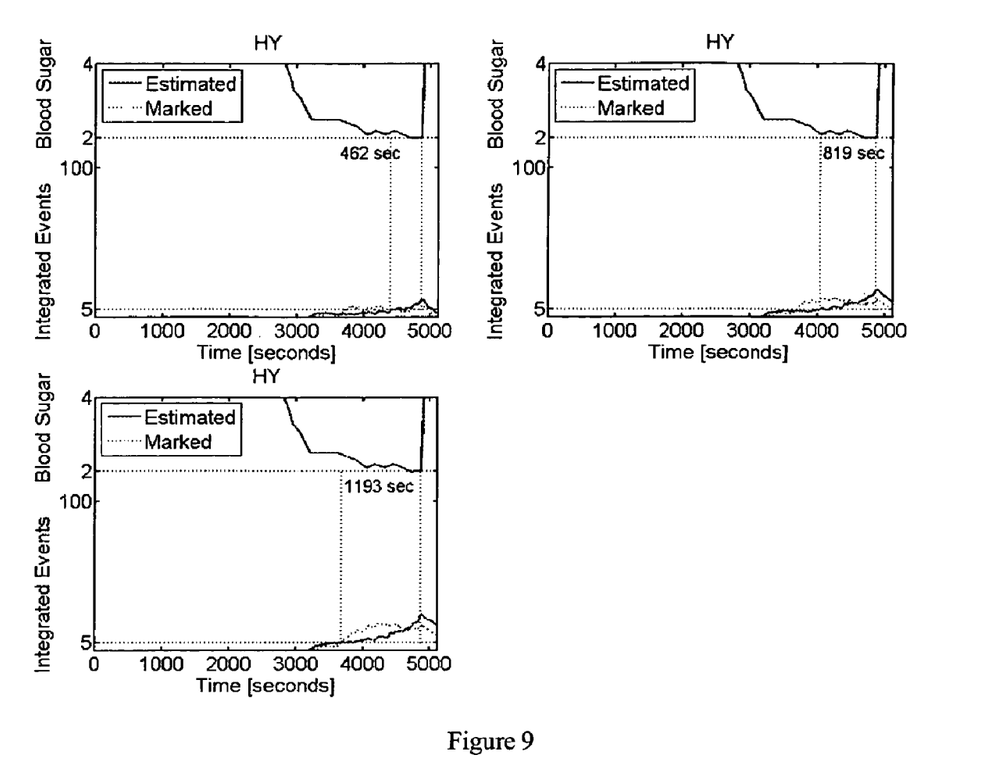
FIG. 9 shows the effect of varying the selected time period on the integration results for one volunteer.

It may be observed however that the integration curve for user HY shows a comparatively gradual rise. The effect on this of adjusting the selected time period for the integration is shown in FIG. 9. Here, the following integration lengths (selected time periods) have been used: 300, 600, and 900 seconds. When comparing the 300 seconds integration (upper left) with the 600 seconds integration (upper right) and the 900 seconds integration (lower left), we see that the longer integration period has produced a curve that looks more similar to the curves for the other 5 subjects as seen in FIG. 7.

Many variations of the apparatus as specifically described may be made within the scope of the invention. For instance, the computation means need not be worn by the user. Especially for use by the bed bound or at night, the computation means may be contained in a separate (e.g. bedside) unit receiving the EEG signals in an unprocessed or partially processed form.

The signal processing and alarm functions can all be accommodated within the implanted unit 14, and that battery power for that may be either rechargeable from an external source of may be of the non-rechargeable type. The alarm signals may be progressively increased as long as an alarm condition is continuously detected. Should the apparatus enter into a state in which it is unable to provide accurate monitoring of the user's gylcaemic status, it may provide a second form of alarm to notify the user of this.

Rather than, or in addition to, an alarm, the apparatus described above for determining the onset of hypoglycaemia may be interlinked with apparatus for administering a blood sugar control substance. For instance, it may be interlinked with an insulin pump to prevent action of the insulin pump when hypoglycaemia is detected, should the insulin pump and its own blood sugar measuring device be malfunctioning.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'.

The invention claimed is:

1. A method for the analysis of EEG signals to detect features therein which are indicative of hypoglycaemia comprising:
dividing EEG signals into a sequence of time segments,
for each time segment determining whether a pattern of EEG signals is present which is indicative of hypoglycaemia and, where a pattern of EEG signals indicative of hypoglycaemia is determined to be present in a time segment, recording this as an event,
integrating the number of events recorded during a selected number of preceding time segments which together constitute a selected time period, and
determining that the EEG signals are indicative that hypoglycaemia is present based on said integration, wherein said integration is performed as a weighted integration in which events detected in time segments further back in time are given a lesser weighting than events detected in more recent time segments.

2. A method as claimed in claim 1, wherein it is determined that the EEG signals are indicative that hypoglycaemia is present when the said integrated number of events exceeds a preset threshold number and/or when there exists a threshold level of matching between a curve of said integration over time and a previously established ideal model of said curve indicative of hypoglycaemia.

3. A method as claimed in claim 1, wherein said weighted integration is performed using a linear weighting function or a sine-curve weighting function.

4. A method as claimed in claim 1, wherein determination of whether a pattern of EEG signals is present in a time segment which is indicative of hypoglycaemia is performed by applying to said signals a previously trained Bayes classifier, a support vector machine (SVM), a relevance vector machine (RVM), a Gaussian process classifier, a classifier based on Fisher's discriminant, a boosted classifier, a naïve Bayes classifier, a K-nearest neighbour classifier, a Binary Decision Tree, a Parzen Window classifier, or a neural network.

5. A method as claimed in claim 4, wherein said determination is carried out using a Bayes Gaussian classifier.

6. A method as claimed in claim 5, wherein during a period of monitoring EEG signals there is carried out a re-estimation of the mean and covariance parameters of the Gaussian model over time.

7. A method as claimed in claim 6, wherein said classifier is a quadratic Bayes Gaussian classifier.

8. A method as claimed in claim 4, wherein a previously trained classifier is applied to said signals which is a classifier trained by supervised learning.

9. A method as claimed in claim 1, wherein raw EEG signals are subjected to spectrum analysis to extract therefrom power averages in at least four frequency bands upon which is based the said determination of whether a pattern of EEG signals is present which is indicative of hypoglycaemia in a time segment of said signals.

10. A method as claimed in claim 9, wherein said at least five frequency bands cover frequencies from 2 Hz to 32 Hz.

11. A method as claimed in claim 10, wherein said frequency bands include bands of approximately (2 Hz-5 Hz), (5 Hz-8 Hz), (8 Hz-11 Hz), (11 Hz-14 Hz), and (14 Hz-32 Hz), wherein all of the boundaries of said frequency bands are variable by up to 20%.

12. A method as claimed in claim 9, wherein prior to said spectrum analysis, artefact or noise elements in said EEG signals are identified and eliminated.

13. A method as claimed in claim 1, wherein said EEG signals have been obtained from one or more electrodes positioned within the area bounded by the FC3-FC1-C1-CP1-P1-P03-P5-CP5-05 standard EEG electrode positions and/or in an equivalent area around C4.

14. A method as claimed in claim 13, wherein the electrodes are positioned within the area bounded by the FC3-FC1-C1-CP1-CP3-05 positions and/or in the equivalent area around C4.

15. A method as claimed in claim 13, wherein the electrodes are positioned within the area bounded by the FC3-C1-CP3-05 positions and/or in the equivalent area around C4.

16. A method as claimed in claim 13, wherein said EEG signals have been obtained from one or more electrodes positioned in at least approximately the C3 and/or C4 or P3 and/or P4 standard EEG electrode positions.

17. A method as claimed in claim 13, wherein said signals are measured with reference to signals obtained from a reference electrode positioned approximately on the frontal-occipital mid-line.

18. A method as claimed in claim 17, wherein said reference electrode is in approximately the Cz or Pz standard EEG electrode position.

19. A method as claimed in claim 1, wherein the time period is adjusted to optimise the sensitivity and specificity of the determination that the obtained signals are indicative of hypoglycaemia for an individual from whom the signals originate.

20. A method as claimed in claim 1, wherein EEG signals are determined to be indicative of hypoglycaemia by establishing that a threshold level of matching between the curve of said integration over time and a previously established ideal model of said curve indicative of hypoglycaemia exists, wherein said matching is carried out by a mathematical convolution of the measured and ideal curves.

21. A method as claimed in claim 1, further comprising activating an alarm upon determination that the EEG signals are indicative of hypoglycaemia.

* * * * *

UNITED STATES PATENT AND TRADEMARK OFFICE
CERTIFICATE OF CORRECTION

PATENT NO. : 8,298,140 B2
APPLICATION NO. : 12/308014
DATED : October 30, 2012
INVENTOR(S) : Henning Beck-Nielsen et al.

Page 1 of 1

It is certified that error appears in the above-identified patent and that said Letters Patent is hereby corrected as shown below:

In claim 13, column 12, line 23, delete "05" and insert --C5--.

In claim 14, column 12, line 27, delete "05" and insert --C5--.

In claim 15, column 12, line 31, delete "05" and insert --C5--.

Signed and Sealed this
Eighteenth Day of December, 2012

David J. Kappos
*Director of the United States Patent and Trademark Office*